United States Patent [19]
Kobayashi et al.

[11] Patent Number: 6,013,773
[45] Date of Patent: Jan. 11, 2000

[54] PHARMACEUTICAL PREPARATION CONTAINING HUMAN GROWTH HORMONE

[75] Inventors: Hideki Kobayashi; Mihoko Aoki; Hiroshi Uchida, all of Chiba-ken; Nobumi Kusuhara, Tokyo; Yukio Miyama, Chiba-ken; Teruo Ito, Chiba-ken; Akira Fukuhara, Chiba-ken; Tsutomu Sato, Chiba-ken, all of Japan

[73] Assignee: Mitsui Chemicals, Inc., Tokyo, Japan

[21] Appl. No.: 08/791,728

[22] Filed: Jan. 31, 1997

[30] Foreign Application Priority Data

Feb. 2, 1996 [JP] Japan ................................. 8-017342

[51] Int. Cl.[7] ..................................................... A61K 37/00
[52] U.S. Cl. ........................ 530/399; 424/44.64; 435/69.4
[58] Field of Search ....................... 424/44.64; 435/69.4; 530/399

[56] References Cited

U.S. PATENT DOCUMENTS

| 4,980,165 | 12/1990 | Isaacs et al. | 424/94.64 |
| 5,496,713 | 3/1996 | Honjo et al. | 435/69.4 |

FOREIGN PATENT DOCUMENTS

| 0303746 | 2/1989 | European Pat. Off. |
| WO90/08557 | 8/1990 | WIPO |
| WO 92/03478 | 3/1992 | WIPO |
| 9312812 | 7/1993 | WIPO |
| WO93/19773 | 10/1993 | WIPO |

OTHER PUBLICATIONS

BIOSIS DN 97128465, Mumenthaler et al., Pharmaceutical Research, 11(1), 12–20. (abstract), 1994.
Abstract 63084500, Patent Abstracts of Japan, vol. 012, No. 312, Aug. 24, 1988.
Rasool et al., Journal of Pharmaceutical Sciences, vol. 80, No. 4, 1991, pp. 387–393.
Gerhard Baumann, "Growth Hormone Heterogeneity: Genes, . . . Proteins"; *Endocrine Reviews*, vol. 12, No. 4 (1991), 424–449.
George E. Chapman et al., "The 20,000 Molecular . . . Hormone"; *The Hournal of Biological Chemistry*, vol. 256, No. 5, (1981), 2395–2401.

*Primary Examiner*—Cecilia J. Tsang
*Assistant Examiner*—C. Delacroix-Muirheid
*Attorney, Agent, or Firm*—Burns, Doane, Swecker & Mathis, L.L.P.

[57] ABSTRACT

A stable pharmaceutical preparation containing a human growth hormone having a molecular weight of about 20,000, or a derivative thereof, can be formulated by adding a water soluble heterocyclic compound, such as creatinine, a salt of acetyltryptophane and nicotinamide, to prevent the insolubilization of the human growth hormone or the derivative thereof in an aqueous solution.

62 Claims, No Drawings

PHARMACEUTICAL PREPARATION CONTAINING HUMAN GROWTH HORMONE

BACKGROUND OF THE INVENTION

1. Field of the Invention

The present invention relates to pharmaceutical preparations containing a human growth hormone having a molecular weight of about 20,000 (hereinafter referred to as 20 k hGH), more specifically to lyophilized preparations prepared from a solution containing 20 k hGH, which have excellent storage stability and do not produce any foreign or insoluble matter when reconstituted, and to processes for the production thereof.

2. Description of the Related Art

There are two known types of human growth hormone: one having a molecular weight of about 22,000 (22 k hGH) and the other having a molecular weight of about 20,000 (20 k hGH). The 22 k hGH is produced by means of recombinant DNA technology and is used for treatment of pituitary dwarfism in the field of pediatrics. The 20 k hGH has never been produced on an industrial scale and it has never been used for medical treatment.

20 k hGH is a single-chain polypeptide having a molecular weight of about 20,000 and has an isoelectric point of about 5.5. Thus, it is stable in an aqueous solution at a neutral pH but unstable at acid and alkaline pH ranges. The solubility of 20 k hGH in aqueous solutions at weak acid to weak alkaline pH ranges is less than about 1 mg/ml and insoluble matter is produced upon thawing out the frozen solution. Thus, 20 k hGH can be considered to be a protein with very low solubility. Furthermore, in aqueous solutions at weak acid to weak alkaline pH ranges, 20 k hGH easily dimerizes. It has been reported that 20 k hGH derived from the human pituitary gland often co-dimerizes or dimerizes with 22 k hGH, a human growth hormone having a molecular weight of about 22,000 (Chapman et al., J. Biol. Chem., Vol. 256, 2395–2401, 1981). These facts suggest that the low solubility of 20 k hGH is due to a hydrophobic interaction of protein molecules.

In order to improve the solubility of highly hydrophobic proteins, sodium dodecyl sulfate, which is extremely surface active, or denaturing agents such as urea and guanidine hydrochloride, and the like are generally used. However, these agents destroy the protein structure, and the primary functions of the proteins will be lost or weakened. Therefore, the use of these conventional agents are not at all preferable if the proteins are to be used in pharmaceutical preparations.

On the other hand, in one known example of the use of solubility promoters to improve the solubility of proteins, equimolar quantities of histidine and creatinine, having a positive charge, and citric acid, having a negative charge, were added to improve the solubility of a modified form of tissue plasminogen activator (hereinafter referred to as tPA) (U.S. Pat. No. 4,980,165). tPA and modified tPA are proteins which are extremely insoluble at neutral pH ranges but highly soluble at acid pH ranges. In other words, the low solubility of tPA and modified tPA is caused by isoelectric precipitation of the proteins, which this method suppresses by the addition of histidine and creatinine, having a positive charge, and citric acid, having a negative charge.

Prescriptions of pharmaceutical preparations containing a human growth hormone having a molecular weight of about 22,000, which are commercially available today, are shown in Table 1. These preparations are generally administered subcutaneously or intramuscularly.

Further, these 22 k hGH preparations primarily contain glycine or mannitol and are stable when stored at 5° C. for 1 year.

TABLE 1

Prescription of commercially available lyophilized 22k hGH

| Name of product | Additive(s) | | Solution reconstitution | |
|---|---|---|---|---|
| Genotropin (Kabi Pharmacia Sumitomo) | 4IU Glycine: | 24 mg | Water for injection | 1 ml |
| Norditropin (Nordisk) | 4IU Glycine: D-Mannitol: | 24 mg 2.4 mg | Water for injection | 1 ml |
| Humatrope (Liliy) | 4IU Glycine: D-Mannitol: | 1.48 mg 7.4 mg | Saline | 2 ml |
| Saizen (Serono) | 4IU D-Mannitol: | 20 mg | Saline | 1 ml |
| Groject (Bio-Tech General) | 4IU D-Mannitol: | 40 mg | Saline | 1 ml |

A study by the present inventors showed that stable preparations could not be obtained when lyophilized 20 k hGH preparations were produced as above.

If a stable aqueous solution of 20 k hGH of sufficient concentration cannot be obtained for use in producing preparations to be administered as described above, then the dosage would have to be increased. This can be extremely inconvenient in the case of 20 k hGH preparations for injection.

Several compounding methods are known to stabilize 22 k human growth hormones in solution. Reported examples include the addition of arginine and EDTA as stabilizing agents for an aqueous 22 k hGH solution (EP Publication No. 639984), the addition of polyhydric alcohols or amino acids in order to control the production of insoluble matter and maintain activity of soluble matter in a 22 k hGH solution (EP 303746), and the addition of histidine as a stabilizing agent in order to suppress an increase in related substances in an aqueous 22 k hGH solution (EP Publication No. 618807). However, all of these methods were developed to stabilize 22 k hGH in a solution, and do not refer to the stabilization of a lyophilized 22 k hGH product. Furthermore, nothing is known about stabilization of a lyophilized preparation of 20 k hGH.

The present inventors studied the solubility and stability of 20 k hGH. As shown in Table 2, the result showed that aside from being of lower molecular weight than 22 k hGH, 20 k hGH is quite different from 22 k hGH in physicochemical properties such as physiological activity, stability and solubility. In particular, the original 20 k hGH bulk solution is unstable even after lyophilization. When its lyophilized preparation is stored at a temperature as low as 5° C., the quantities of related substances, such as a deamidated variant in which $Asp^{134}$ in 20 k hGH is deamidated to $Asp^{134}$ and a sulfoxide variant in which $Met^{14}$ was converted to ox-$Met^4$, and high molecular weight polymer products, increased over time. The related substances means, for example, a mono-deamidated variant in which $Asn^{134}$ in 20 k hGH is deamidated to $Asp^{134}$, a di-deamidated variant in which besides $Asn^{134}$, $Asn^{137}$ was also deamidated, and a sulfoxide variant in which $Met^{14}$ was converted to ox-$Met^{14}$. Furthermore, in handling, for example, pipetting, a solution in which the 20 k hGH was dissolved, the protein were readily aggregated to produce insoluble matter. In other words, the stability in an aqueous solution is low. As described hereinafter, even the addition of basic amino acids to a 20 k hGH solution does not suppress the production of insoluble matter or related substances. As discussed above, 20 k hGH is highly hydrophobic, which may explain why it tends to produce more insoluble matter than 22 k hGH.

TABLE 2

Difference in physicochemical properties between 20k hGH and 22k hGH

| Physicochemical property | 20k hGH | 22k hGH |
| --- | --- | --- |
| Isoelectric point | pH 5.5[1] | pH 5.1[1] |
| Dimer formation | Easily formed[2] | Hardly formed[2] |
| Hydrophobicity | High[3] | Low[3] |
| Solubility in water | Low[3] | High[3] |
| Stability of lyophilized hGH | Low[3] | High[3] |
| Stability of dissolved hGH | Low[3] | High[3] |

[1]: Endocrine Reviews, Vol. 12, 314–324, 1991.
[2]: J. Biol. Chem., Vol. 256, 2395–2401, 1981.
[3]: Data by the present inventors.

SUMMARY OF THE INVENTION

As described above, it is very difficult to obtain a solution in which 20 k hGH maintains its physiological activity in a soluble and stable form simply, by applying the conventional compounding preparations of 22 k hGH. Accordingly, there is a strong need to develop new compounding prescriptions for stable 20 k hGH pharmaceutical preparations which retain an appropriate concentration for injection.

Furthermore, since lyophilization of 20 k hGH alone cannot prevent the production of related substances and high molecular weight polymer products, there is a need to develop a stable lyophilized pharmaceutical preparations containing 20 k hGH, which produce very little related substances or high molecular weight polymer products.

Accordingly, an object of the present invention is to provide pharmaceutical preparations which contain 20 k hGH and produce very little insoluble matter derived from the 20 k hGH when dissolved in water. Another object of the present invention is to provide lyophilized preparations containing 20 k hGH which suppressed the production of related substances and high molecular weight polymer products after reconstitution.

An additional object of the present invention is to provide methods to prevent the insolubilization of 20 k hGH in a pharmaceutical preparation containing 20 k hGH in order to improve its stability, and a method to suppress the production of related substances and high molecular weight polymer products over time in a lyophilized preparation containing 20 k hGH.

The present inventors did extensive studies to achieve the abovementioned objective, that is, to improve the solubility and stability of 20 k hGH and to provide a compounding prescription for a stable 20 k hGH preparation upon lyophilization. As a result, the present inventors have succeeded in producing a pharmaceutical preparation containing 20 k hGH which has excellent solubility and stability.

Furthermore, the present inventors found that when a basic amino acid and a nonionic surfactant are added to a lyophilized preparation containing 20 k hGH, the production of related substances of the lyophilized preparation was suppressed to improve stability, such that said lyophilized preparation did not produce any insoluble matter when reconstituted in water; thereby completing the present invention.

Namely, the present invention comprises pharmaceutical preparations containing a human growth hormone having a molecular weight of about 20,000, or a derivative thereof, and a water soluble heterocyclic compound; methods to prevent insolubilization of a human growth hormone having a molecular weight of about 20,000, or a derivative thereof, thereby improving the stability of a pharmaceutical preparation containing said human growth hormone or a derivative thereof by adding a water soluble heterocyclic compound; and methods to suppress the production of related substances over time in a lyophilized preparation containing a human growth hormone having a molecular weight of about 20,000, or a derivative thereof, by adding one or two kinds of basic amino acids, or salts thereof, and a nonionic surfactant.

The present inventors found that the solubility of 20 k hGH can be improved by adding a water soluble heterocyclic compound, such as creatinine, in a certain concentration to a 20 k hGH preparation in which the use of buffer solutions generally used for physiological substances would not provide a sufficient concentration of 20 k hGH for use as a pharmaceutical preparation.

Furthermore, it is possible to prevent the production of extremely small amounts of insoluble matter by controlling the pH of an aqueous 20 k hGH. It was also found that the stability in solution upon thawing can be improved by adding a nonionic surfactant such as polysorbate 80, and furthermore, stability upon lyophylized preparation and during reconstitution can be improved by adding basic amino acids and mannitol, a sugar alcohol. These findings readily enable the mass production of pharmaceutical preparations containing lyophilized 20 k hGH which can be reconstitution to prepare aqueous solutions suitable for injection.

DETAILED DESCRIPTION OF THE INVENTION AND PREFERRED EMBODIMENTS

The growth hormone according to the present invention is a human growth hormone having a molecular weight of about 20,000 (20 kHG) and said human growth hormone can be either a natural hormone or one obtained by means of recombinant DNA technology.

Examples of the 20 k hGH according to the present invention include those having amino acid sequences shown below, i.e., SEQ ID NO: 1 and SEQ ID NO: 2; however, those in which one or several amino acids in the entire amino acid sequence of SEQ ID NO: 1 or SEQ ID NO: 2 are different are also within the scope of the invention as long as the resultant 20 k hGH has retained its physiological characteristics.

```
Phe Pro Thr Ile Pro Leu Ser Arg Leu Phe Asp Asn Ala Met Leu  SEQ ID NO: 1
 1           5                  10                  15

Arg Ala His Arg Leu His Gln Leu Ala Phe Asp Thr Tyr Gln Glu
            20                  25                  30
```

```
                                    -continued
Phe Asn Pro Gln Thr Ser Leu Cys Phe Ser Glu Ser Ile Pro Thr
                35              40              45

Pro Ser Asn Arg Glu Glu Thr Gln Gln Lys Ser Asn Leu Glu Leu
                50              55              60

Leu Arg Ile Ser Leu Leu Leu Ile Gln Ser Trp Leu Glu Pro Val
                65              70              75

Gln Phe Leu Arg Ser Val Phe Ala Asn Ser Leu Val Tyr Gly Ala
                80              85              90

Ser Asp Ser Asn Val Tyr Asp Leu Leu Lys Asp Leu Glu Glu Gly
                95              100             105

Ile Gln Thr Leu Met Gly Arg Leu Glu Asp Gly Ser Pro Arg Thr
                110             115             120

Gly Gln Ile Phe Lys Gln Thr Tyr Ser Lys Phe Asp Thr Asn Ser
                125             130             135

His Asn Asp Asp Ala Leu Leu Lys Asn Tyr Gly Leu Leu Tyr Cys
                140             145             150

Phe Arg Lys Asp Met Asp Lys Val Glu Thr Phe Leu Arg Ile Val
                155             160             165

Gln Cys Arg Ser Val Glu Gly Ser Cys Gly Phe
                170             175

Phe Pro Thr Ile Pro Leu Ser Arg Leu Phe Asp Asn Ala Met Leu   SEQ ID NO: 2
 1               5              10              15

Arg Ala His Arg Leu His Gln Leu Ala Phe Asp Thr Tyr Gln Glu
                20              25              30

Phe Asn Pro Gln Thr Ser Leu Cys Phe Ser Glu Ser Ile Pro Thr
                35              40              45

Pro Ser Asn Arg Glu Glu Thr Gln Gln Lys Ser Asn Leu Glu Leu
                50              55              60

Leu Arg Ile Ser Leu Leu Leu Ile Gln Ser Trp Leu Glu Pro Val
                65              70              75

Gln Phe Leu Arg Ser Val Phe Ala Asn Ser Leu Val Tyr Gly Ala
                80              85              90

Ser Asp Ser Asn Val Tyr Asp Leu Leu Lys Asp Leu Glu Glu Gly
                95              100             105

Ile Gln Thr Leu Met Gly Arg Leu Glu Asp Gly Ser Pro Arg Thr
                110             115             120

Gly Gln Ile Phe Lys Gln Thr Tyr Ser Lys Phe Asp Thr Asn Ser
                125             130             135

His Asn Asp Asp Ala Leu Leu Lys Asn Tyr Gly Leu Leu Tyr Cys
                140             145             150

Phe Arg Lys Asp Met Asp Lys Val Glu Thr Phe Leu Arg Ile Val
                155             160             165

Gln Cys Arg Ser Val Glu Gly Ser Cys Gly Phe
                170             175
```

The concentration of 20 k hGH contained in a pharmaceutical preparation containing 20 k hGH according to the present invention is 0.5 to 10.0 mg/ml, preferably 1.0 to 3.0 mg/ml, more preferably 1.5 to 2.5 mg/ml, before lyophilization. Furthermore, effective concentrations of 20 k hGH in reconstituted solutions of lyophilized preparations is less than 10 mg/ml.

Pharmaceutical preparations containing 20 k hGH of the present invention contain a water soluble heterocyclic compound in order to improve the solubility of 20 k hGH in a solution of the preparation, and in a solution of a reconstituted lyophilized preparation. The water soluble heterocyclic compound to be used in the present invention is one or more of the compounds selected from the group consisting of creatinine, a salt of acetyltryptophane such as sodium acetyltryptophane and nicotinamide; however, creatinine is preferable. The concentration of said water soluble heterocyclic compound in a solution of the preparation or in a solution of a reconstituted lyophilized preparation is 0.1% to 10%, preferably 0.3% to 5%.

The pH of a pharmaceutical preparation containing 20 k hGH of the present invention is 5 to 8, preferably 6.0 to 7.8, more preferably 6.5 to 7.6.

When pH adjustment is necessary, a simple pH adjusting agent, such as hydrochloric acid, phosphoric acid and sulfuric acid can be used, or a buffer solution such as tris (hydroxymethyl)aminomethane, phosphoric acid, maleic acid, succinic acid, citric acid, acetic acid, histidine or salts thereof can be used. Phosphoric acid, or a salt thereof, is preferable. The concentration of said buffer solution is 0.1 mM to 100 mM, preferably 5 mM to 50 mM.

The basic amino acids which may be used in the lyophilized preparation containing 20 k hGH of the present invention are, for example, lysine, histidine, arginine or salts thereof. The amount of the basic amino acid to be added is 1 to 20 parts by weight to 1 part by weight of 20 k hGH, preferably 2 to 15 parts by weight.

Furthermore, lyophilized preparations containing 20 k hGH according to the present invention may contain a nonionic surfactant to improve the stability of 20 k hGH after reconstitution of said lyophilized preparation. The nonionic surfactants to be used in the present invention are polyoxyethylenepolyoxypropyleneglycol and polysorbate, e.g., polyoxyethylene (160) polyoxypropylene (30) glycol, polysorbate 20 or polysorbate 80. Polysorbate 20 or polysorbate 80, or both are preferable. Polysorbate 80 is more preferable. The concentration of nonionic surfactant in a solution of a reconstituted lyophilized preparation is 0.02% to 1%, preferably 0.02% to 0.2%.

Furthermore, lyophilized preparations containing 20 k hGH of the present invention can be compounded with an excipient to improve the appearance of the cake upon lyophilization. An example of the excipient is a sugar alcohol, e.g., mannitol. The concentration of said excipient is 0.1% to 5%, preferably 0.5% to 2%, in a solution of a reconstituted lyophilized preparation.

The pH of pharmaceutical preparations of the present invention can be adjusted after adding a diluted solution of 20 k hGH to an aqueous solution supplemented with the abovementioned water soluble heterocyclic compound.

Furthermore, it is preferable to convert the pharmaceutical preparations of the present invention into lyophilized produced. There are no restrictions as to methods and conditions for producing the lyophilized preparation. For example, lyophilization can be carried out by adding a diluted 20 k hGH solution to an aqueous solution supplemented with a water soluble heterocyclic compound of the abovementioned concentration, and optionally a specified amount of basic amino acid, a nonionic surfactant, and an excipient, if necessary, adjusting the pH, freezing the resulting admixture at −30° C. to −80° C., and then drying under reduced pressure by a conventional method.

Furthermore, when pharmaceutical preparations of the present invention are used for injections, the lyophilized preparations may be reconstituted with appropriate water for injections or solutions containing osmotic pressure adjustmenting agents such as sodium chloride or dextrose or sugar alcohols.

The present invention will be explained in more detail by the following examples; however, the present invention is not limited to those examples.

EXAMPLE 1

Effect of Addition of Creatinine on Solubility of 20 k hGH 20 k hGH used in Examples 1 to 9 was prepared by means of recombinant DNA technology. More specifically, it was prepared according to the method described in U.S. Pat. No. 5,496,713 using a transformant strain, MT-10765 (deposited with Accession Number FERM BP-5020 at the National Institute of Bioscience and Human-Technology of the Agency of Industrial Science & Technology of the Ministry of International Trade and Industry according to the Budapest Treaty; Deposition Date; Feb. 28, 1995). Namely, an expression and secretion plasmid carrying the gene encoding 20 k hGH was introduced in *Escherichia coli* and the resulting transformant, MT-10765, was cultured in a medium containing polypeptone, yeast extract, glycerol, etc. After completing the culture, the bacterial cells were harvested by centrifugation and the outer membranes of the cells were burst by the osmotic shock method to recover the periplasm fraction only. Isolation and purification of 20 k hGH from the periplasm fraction were carried out according to known methods or their variations.

Urea was added to an aqueous solution containing 0.2 mg/ml to 0.4 mg/ml of 20 k hGH obtained as above, and the admixture was concentrated to about 8 mg/ml. Portions of the resultant concentrated solution were added to gel filtration columns each equilibrated with a 20 mM sodium phosphate buffer solution (pH 6.5) containing creatinine in concentrations of 0%, 0.3% (27.8 mM), 0.6% (55.5 mM), 1.25% (11.1 mM), 2.5% (221 mM) and 5% (442 mM), respectively. Urea was removed by gel filtration and the purified fractions were eluted by being replaced by 20 mM sodium phosphate buffer containing creatinine at the abovementioned, various concentrations, respectively. The protein concentration of each purified fraction was measured and change in appearance of solution of the fractions was visually evaluated. The effect of the addition of creatinine are shown in Table 3. From the results in Table 3, it was confirmed that creatinine in the solution improved the solubility of 20 k hGH, and furthermore, the concentration of 20 k hGH in the purified fractions obtained by gel filtration increased with an increase in the creatinine concentration. Evaluation of other heterocyclic compounds to be used in the present invention, i.e., sodium acetyltryptophane and nicotinamide, showed that they have similar effects as creatinine.

Furthermore, similar results were obtained when an experiment was carried out using 20 k hGH which was obtained using the transformant MT-10712 (deposited with the Accession Number FERM BP-4361 at the National Institute of Bioscience and Human-Technology of the Agency of Industrial Science & Technology of the Ministry of International Trade and Industry according to the Budapest Treaty; Deposition Date: Jul. 12, 1993), by the same procedure as described above.

These results showed that the addition of creatinine was effective without the addition of an equimolar amount of a negative charged compound. This suggests that the addition of creatinine in affecting the solubility of 20 k hGH is not caused by preventing isoelectric precipitation.

TABLE 3

| Effect of addition of creatinine on solubility of 20k hGH | | |
|---|---|---|
| Creatinine | Purified fraction from gel filtration | |
| concentration in solution (%) | appearance of solution | Concentration (mg/ml) |
| 0 | + | Not measured |
| 0.3 | − | 2.9 |

TABLE 3-continued

Effect of addition of creatinine on solubility of 20k hGH

| Creatinine concentration in solution (%) | Purified fraction from gel filtration | |
|---|---|---|
| | appearance of solution | Concentration (mg/ml) |
| 0.6 | − | 3.1 |
| 1.25 | − | 4.1 |
| 2.5 | − | 4.5 |
| 5.0 | − | 4.8 |

Note:
+: precipitates produced; −: clear.

EXAMPLE 2
Effect of Addition of Polysorbate 80 on the Appearance of Solution of 20 k hGH Aqueous Solution After Freezing/Thawing Polysorbate 80 (commercial name: Tween 80) was added individually at a concentration of 0, 0.005, 0.01, 0.02, 0.05, 0.1 and 0.2% to the 20 k hGH solution containing 1.25% (111 mM) of creatinine as shown in Table 3 above. The visual change in each 20 k hGH solution before freezing and after thawing was observed in a container having four sides made of clear glass under 6,000 luxes of fluorescent lamp. The 20 k hGH concentration used was about 2 mg/ml. The effect of the addition of polysorbate 80 is shown in Table 4. Results revealed that the addition of polysorbate 80 at a concentration of more than 0.02% prevented the production of small amounts of insoluble matter of 20 k hGH caused by freezing and thawing, and thus proving that the solution remains stable.

TABLE 4

Effect of addition of polysorbate 80 on solubility of 20k hGH after freezing/thawing

| Concentration of polysorbate 80 in solution (%) | Change in appearance of solution before freezing and after thawing of 20k hGH aqueous solution | |
|---|---|---|
| | Before freezing | After thawing |
| 0 | − | ++ |
| 0.005 | − | + |
| 0.01 | − | + |
| 0.02 | − | − |
| 0.05 | − | − |
| 0.1 | − | − |
| 0.2 | − | − |

Note:
−: Clear; +: with slightly insoluble matter; ++: with obviously insoluble matter.

EXAMPLE 3
Effects of Addition of Mannitol on Appearance of both 20 k hGH Lyophilized Cake and of Solution After Reconstitution Mannitol, as an excipient, was added at a concentration of 0, 1.0 and 5.0% to aqueous solutions of 20 k hGH which contained polysorbate 80 at a concentration of 0.05% and 0.2% as shown in Table 4 and creatinine at a concentration of 1.25% (111 mM), respectively. The admixtures were dispensed into separate vials, which were cooled from 5° C. to −40° C., and then frozen at −40° C. for 5 hours. The temperature was then raised from −40° C. to −25° C. under reduced pressure, after which the vials were dried under reduced pressure at −25° C. for another 60 hours. Next, the temperature was increased to 15° C. under reduced pressure, and the vials were dried at this temperature for 6 hours. After observing the appearance of the resulting lyophilized cakes, 1 ml of distilled water for injection was added to each cake to observe the appearance of the reconstituted solution under 6,000 luxes of fluorescent lighting. The effect of the addition of mannitol is shown in Table 5. Results in Table 5 show that the appearance and formability of the lyophilized cakes are improved by the addition of mannitol. Furthermore, it is confirmed that reconstitution is excellent without insoluble matter.

TABLE 5

Effects of addition of mannitol on appearance of both lyophilized preparation of 20k hGH and of solution after reconstituion

| Concentrations of solvent composition (%) | | | Appearance of lyophilized cake | Appearance of solution after reconstitution |
|---|---|---|---|---|
| Creatinine | Polysorbate 80 | Mannitol | | |
| 1.25 | 0 | 0 | Δ | ++ |
| 1.25 | 0.05 | 0 | ○ | − |
| 1.25 | 0.05 | 1.0 | ⊚ | − |
| 1.25 | 0.05 | 5.0 | ⊚ | − |
| 1.25 | 0.2 | 0 | ○ | − |
| 1.25 | 0.2 | 1.0 | ⊚ | − |
| 1.25 | 0.2 | 5.0 | ⊚ | − |

Note:
−: clear; +: with minor insoluble matter; ++: with clearly visible insoluble matter; Δ: slightly poor; 0: good; O: excellent.

EXAMPLE 4
Effect of Addition of Basic Amino Acids and/or Mannitol on Production of Insoluble Matter After Reconstitution of 20 k hGH Lyophilized Preparation Aqueous solutions containing 2 mg/ml of 20 k hGH, specified amounts of basic amino acid or hydrochloride thereof, 1.25% (111 mM) creatinine, 2.5% mannitol and 0.05% polysorbate 80, having a pH 7.6 adjusted with sodium dihydrogenphosphate and sodium hydroxide, were prepared. Then, 1 ml portions of the solutions were dispensed into vials, which were cooled from 5° C. to −40° C., and then frozen at −40° C. for 5 hours. The temperature was then raised from −40° C. to −25° C. under reduced pressure, after which the vials were dried under reduced pressure at −25° C. for another 60 hours. Next, the temperature was increased to 15° C. under reduced pressure, and the vials were dried at this temperature for 6 hours. The resulting lyophilized preparations were reconstituted with 1 ml of distilled water for injection and stored at 5° C. for 7 days. The state of solution at day 0 and day 7 was observed under 6,000 luxes of fluorescent lamp. Results are shown in Table 6.

TABLE 6

Effect of basic amino acids on production of insoluble matters in solution

| Basic amino acid/mannitol | Amount | | State of solution | |
|---|---|---|---|---|
| Amino acid | added (mg) | pH | Day 0 | Day 7 |
| — | 0 | 6.5 | − | + |
| — | 0 | 7.6 | − | − |
| Arginine hydrochloride | 4.2 | 7.6 | − | + |
| Arginine hydrochloride | 6.0 | 7.6 | − | + |
| Arginine hydro-chloride + mannitol | 4.2 | 7.6 | − | − |

TABLE 6-continued

Effect of basic amino acids on production of insoluble matters in solution

| Basic amino acid/mannitol | Amount | | State of solution | |
|---|---|---|---|---|
| Amino acid | added (mg) | pH | Day 0 | Day 7 |
| Arginine hydrochloride + mannitol | 6.0 | 7.6 | – | – |
| Histidine | 6.0 | 7.6 | – | + |
| Lysine hydrochloride | 6.0 | 7.6 | – | + |

Note:
–: clear; ±: with very little insoluble matter; +: with little insoluble matter; ++: with clearly visible insoluble matter.

As shown in Table 6, basic amino acids did not suppress the production of insoluble matter in a 20 k hGH solution, and instead had a detrimental effect. These results confirmed that the production of insoluble matter was suppressed by adding mannitol and controlling the pH.

EXAMPLE 5
Effect of Addition of Basic Amino Acids on Increasing Related Substances in Solution After Reconstitution of 20 k hGH Lyophilized Preparation An experiment was carried out in the same manner as described in Example 4, except that the pH of an aqueous solution containing 20 k hGH was adjusted to 7.6. Related substances (deamidated variants and sulfoxide variants) were qualitatively measured by liquid chromatography on day 0 and day 7. Results are shown in Table 7.

TABLE 7

Effect of basic amino acids on production of related substances

| Basic amino acid added | Amount added | | Analogous substances (%) | | |
|---|---|---|---|---|---|
| Amino acid | (mg) | pH | Day 0 | Day 7 | Increase |
| — | 0 | 7.6 | 5.1 | 5.4 | 0.3 |
| Arginine hydrochloride | 4.2 | 7.6 | 5.1 | 5.5 | 0.4 |
| Arginine hydrochloride | 6.0 | 7.6 | 5.1 | 5.5 | 0.4 |
| Histidine | 6.0 | 7.6 | 5.2 | 5.5 | 0.3 |
| Lysine hydrochloride | 6.0 | 7.6 | 5.2 | 5.6 | 0.4 |

As shown in Table 7, the addition of basic amino acids had no effect, and neither increased nor decreased the amount of related substances in solution.

EXAMPLE 6
Effect of Addition of Arginine and Arginine Hydrochloride on Increase in Related Substances in 20 k hGH Lyophilized Preparation Aqueous solutions each containing 2 mg/ml of 20 k hGH, specified amounts of arginine or arginine hydrochloride, 1.25% (111 mM) creatinine, 0.05% polysorbate 80, having a pH adjusted to 7.6 with sodium dihydrogenphosphate and sodium hydroxide, were prepared. Then, 1 ml portions of the solutions were dispensed into vials, which were cooled from 5° C. to –40° C., and then frozen at –40° C. for 5 hours. The temperature was then raised from –40° C. to –25° C. under reduced pressure, after which the vials were dried under reduced pressure at –25° C. for another 60 hours. Next, the temperature was increased to 15° C. under reduced pressure, and the vials were dried at this temperature for 6 hours. The resulting lyophilized preparations were stored at 40° C. for 2 weeks. Concentrations of related substances were measured at day 0 and 2 weeks later by liquid chromatography. Results are shown in Table 8.

As shown in Table 8, the addition of arginine or arginine hydrochloride suppressed the production of related substances.

TABLE 8

Effect of addition of arginine or arginine hydrochloride on production of related substances in lyophilized preparation

| | | Analogous substance (%) | | |
|---|---|---|---|---|
| Basic amino acids Amino acid | Amount added (mg) | Day 0 | After 2 weeks | Increase |
| — | 0 | 3.9 | 10.7 | 6.8 |
| Arginine hydrochloride | 1.05 | 3.7 | 7.0 | 3.3 |
| Arginine hydrochloride | 4.20 | 3.8 | 5.6 | 2.2 |
| Arginine hydrochloride | 6.00 | 3.7 | 5.5 | 1.8 |
| Arginine hydrochloride | 26.7 | 7.6 | 8.2 | 0.6 |
| Arginine | 4.96 | 3.9 | 7.0 | 3.1 |

EXAMPLE 7
Effect of Addition of Lysine Hydrochloride and Histidine on Increase in Related Substances in 20 k hGH Lyophilized Preparation Aqueous solutions each containing 2 mg/ml of 20 k hGH, specified amounts of lysine hydrochloride or histidine, 1.25% creatinine, 0.05% polysorbate 80, having a pH adjusted to 7.6 with sodium dihydrogenphosphate and sodium hydroxide, were prepared. Then, 1 ml portions of the solutions were dispensed into vials, which were cooled from 5° C. to –40° C., and then frozen at –40° C. for 5 hours. The temperature was then raised from –40° C. to –25° C. under reduced pressure, after which the vials were dried under reduced pressure at –25° C. for another 60 hours. Next, the temperature was increased to 15° C. under reduced pressure, and the vials were dried at this temperature for 6 hours. The resulting lyophilized preparations were stored at 40° C. for 2 weeks. Concentrations of related substances were measured at day 0 and 2 weeks later by liquid chromatography. Results are shown in Table 9.

As shown in Table 9, the addition of a basic amino acid and salt thereof, i.e., histidine and lysine hydrochloride affected to suppress the production of related substances in the same manner as the abovementioned arginine and arginine hydrochloride.

TABLE 9

Effect of addition of basic amino acid on production of related substances in lyophilized preparation

| | | Related substance (%) | | |
|---|---|---|---|---|
| Basic amino acids Amino acid | Amount added (%) | Day 0 | After 2 weeks | Increase |
| — | 0 | 3.9 | 10.7 | 6.8 |
| Histidine | 4.4 | 3.8 | 5.8 | 2.0 |
| Lysine hydrochloride | 5.2 | 3.9 | 5.6 | 1.8 |

EXAMPLE 8
Effect of Addition of Basic Amino Acids on Increase in High Molecular Weight Polymer Products in 20 k hGH Lyophilized preparation Aqueous solutions each containing 2 mg/ml of 20 k hGH, specified amounts of basic amino acids, 1.25% creatinine, 0.05% polysorbate 80, having a pH adjusted to 7.6 with sodium dihydrogenphosphate and sodium hydroxide, were prepared. Then, 1 ml portions of the solutions were dispensed into vials, which were cooled from 5° C. to −40° C., and then frozen at −40° C. for 5 hours. The temperature was then raised from −40° C. to −25° C. under reduced pressure, after which the vials were dried under reduced pressure at −25° C. for another 60 hours. Next, the temperature was increased to 15° C. under reduced pressure, and the vials were dried at this temperature for 6 hours. The resulting lyophilized preparations were stored at 40° C. for 2 weeks. Concentrations of high molecular weight polymer products were assayed by electrophoresis (SDS-PAGE) at day 0 and 2 weeks later. Namely, the lyophilized preparations in the vials were dissolved with water for injection and heated for 3 minutes with and without a reducing agent (mercaptoethanol) in a boiling water bath. Each sample solution was added (10 µg per well) to a polyacrylamide gradient gel for electrophoresis at constant current with subsequent silver staining. Results are shown in Table 10.

As shown in Table 10, the addition of basic amino acids suppresses the production of high molecular weight polymer products.

TABLE 10

Effect of addition of basic amino acid on production of high molecular weight polymer products in lyophilized preparation

| Basic amino acids Amino acid | Amount added (mg) | High molecular weight polymer products (after 2 weeks) | |
|---|---|---|---|
| | | Unreduced | Reduced |
| None | 0 | +++ | ++ |
| Arginine hydrochloride | 2.1 | ++ | + |
| Arginine hydrochloride | 4.20 | + | ± |
| Arginine hydrochloride | 6.00 | ± | − |
| Arginine hydrochloride | 26.7 | − | − |
| Arginine | 6.0 | + | ± |
| Lysine hydrochloride | 5.2 | + | ± |
| Histidine | 4.4 | + | ± |

Shade of bands on SDS-PAGE for high molecular weight polymer products
- +++: densely shaded; ++: distinctly shaded; +: shaded, ±: slightly shaded; −: not shaded.

EXAMPLE 9

20 k hGH Lyophilized Preparation

A solution (560 ml) containing 20 k hGH (2 mg/ml), creatinine (1.25%, 111 mM) and polysorbate 80 (0.05%), which had been kept frozen, was allowed to thaw in running water and filtered through a 0.22 µm filter. 15 g of D-mannitol and 5.52 g of arginine hydrochloride were added to 510 ml of this filtrate, and dissolved over ice using a stirring bar. About 14 ml of a 0.5 N sodium hydroxide solution were then added to this solution over ice to adjust the pH to 7.6, after which purified water was added to make the total volume to exactly 600 ml. Using a vial-injection dispenser, 1 ml portions of this solution were dispensed into 2 ml glass vials, which were then lyophilized. For this, the shelf temperature was rapidly decreased from 5° C. to −40° C., and preliminary freezing was carried out at −40° C. for 5 hours, after which the vials were dried under reduced pressure at a shelf temperature of −25° C. for about 50 hours. Next, the shelf temperature was maintained at 15° C. under reduced pressure, then the vials were dried for 6 hours to obtain a lyophilized preparation. The resulting cake of the lyophilized preparation had good features, and a clear solution was obtained when reconstituted with injection grade distilled water. The lyophilized preparation was stored at 40° C. for 2 months. During storage, the change in appearance of cake and the solution after reconstituted were evaluated, and the amount of related substances was measured. Results are shown in Table 11.

Results confirm that this lyophilized preparation have good appearance, produces no insoluble matter, suppress the production of related substances and contains stable 20 k hGH, even after prolonged storage.

TABLE 11

Stability test of lyophilized preparation

| | Appearance | Appearance of reconstituted solution and related substance (%) | |
|---|---|---|---|
| Day 0 | Good | Clear | 3.9 |
| After 4 weeks | Good | Clear | 5.6 |
| After 8 weeks | Good | Clear | 6.2 |

What is claimed is:

1. A stable pharmaceutical preparation which comprises an aqueous solution containing a pharmaceutically effective amount of a human growth hormone having a molecular weight of about 20,000, and further comprising an amount of at least one compound selected from the group consisting of creatinine, an acetyl tryptophan salt, and nicotinamide, sufficient to enhance the solubility of said human growth hormone.

2. The stable pharmaceutical preparation of claim 1, wherein said compound is creatinine.

3. The stable pharmaceutical preparation of claim 1, which further comprises a nonionic surfactant.

4. The stable pharmaceutical preparation of claim 3, wherein said nonionic surfactant is polysorbate 20 or polysorbate 80.

5. The stable pharmaceutical preparation of claim 1, which comprises an aqueous solution having a pH ranging from 5 to 8.

6. The stable pharmaceutical composition of claim 5, wherein pH is controlled by the addition of a buffer or a pH controlling agent.

7. A method for producing an aqueous pharmaceutical preparation suitable for human administration comprising a human growth hormone having a molecular weight of about 20,000 having reduced insoluble matter, comprising adding to said pharmaceutical composition a compound selected from the group consisting of creatinine, an acetyl tryptophan salt, and nicotinamide in an amount sufficient to reduce the amount of insoluble matter contained therein.

8. The method of claim 7, wherein said compound is creatinine.

9. The method of claim 8, wherein said pharmaceutical preparation comprises a pH ranging from 5 to 8.

10. A stable pharmaceutical preparation comprising a human growth hormone having a molecular weight of about 20,000, said preparation comprising (i) a pharmaceutically effective amount of a human growth hormone having a molecular weight of about 20,000; (ii) arginine; (iii) polysorbate; and (iv) mannitol, wherein the amounts of (ii), (iii) and (iv) are sufficient to enhance the stability and solubility of said human growth hormone in said preparation.

11. A stable lyophilized preparation which comprises a human growth hormone having a molecular weight of about 20,000, and an amount of at least one water-soluble heterocyclic compound sufficient to enhance the stability of said human growth hormone and at least one basic amino acid or salt thereof in an amount sufficient to reduce the production of deamidated and sulfoxide variants of said human growth hormone.

12. The stable lyophilized preparation of claim 11, wherein said at least one water-soluble heterocyclic compound is selected from the group consisting of creatinine, an acetyl tryptophan salt, and nicotinamide.

13. The stable lyophilized preparation of claim 12, wherein said at least one water-soluble heterocyclic compound is creatinine.

14. The stable lyophilized preparation of claim 11, which further comprises at least one basic amino acid or salt thereof.

15. The stable lyophilized preparation of claim 14, wherein said at least one basic amino acid or salt thereof is selected from the group consisting of arginine, arginine hydrochloride, lysine, lysine hydrochloride, and histidine.

16. The stable lyophilized preparation of claim 14, which comprises 1 to 20 parts by weight of said basic amino acid or salt thereof, and 1 part by weight of said human growth hormone having a molecular weight of about 20,000.

17. The stable lyophilized preparation of claim 11, which further comprises a nonionic surfactant.

18. The stable lyophilized preparation of claim 17, wherein said nonionic surfactant is polysorbate 20 or polysorbate 80.

19. The stable lyophilized preparation of claim 11, which further comprises an excipient.

20. The stable lyophilized preparation of claim 11, wherein said excipient is a sugar alcohol.

21. The stable lyophilized preparation of claim 20, wherein said sugar alcohol is mannitol.

22. A reconstituted human growth hormone preparation produced by adding water or an aqueous solution to the stable lyophilized preparation of claim 11.

23. The reconstituted human growth hormone preparation of claim 22, said preparation having a pH ranging from 5 to 8.

24. A stable lyophilized preparation which comprises a human growth hormone having a molecular weight of about 20,000, said preparation comprising (i) a pharmaceutically effective amount of a human growth hormone having a molecular weight of about 20,000, (ii) creatinine; (iii) arginine; (iv) polysorbate 20 or polysorbate 80; and (v) mannitol, wherein the amounts of (ii), (iii), (iv) and (v) are sufficient to enhance the stability and solubility of said human growth hormone (i) in said preparation.

25. A stable pharmaceutical preparation which comprises an aqueous solution containing a pharmaceutically effective amount of a human growth hormone having a molecular weight of about 20,000, and an amount of at least one water-soluble heterocyclic compound sufficient to enhance the stability of said human growth hormone and at least one basic amino acid or salt thereof in an amount sufficient to reduce the production of deamidated and sulfoxide variants of said human growth hormone.

26. The stable pharmaceutical preparation of claim 25, wherein said at least one water-soluble heterocyclic compound is selected from the group consisting of creatinine, an acetyl tryptophan salt, and nicotinamide.

27. The stable pharmaceutical preparation of claim 25, wherein said at least one water-soluble heterocyclic compound is creatinine.

28. The stable pharmaceutical preparation of claim 25, which further comprises at least one basic amino acid or salt thereof.

29. The stable pharmaceutical preparation of claim 28, wherein said at least one basic amino acid or salt thereof is selected from the group consisting of arginine, arginine hydrochloride, lysine, lysine hydrochloride, and histidine.

30. The stable pharmaceutical preparation of claim 28, which comprises 1 to 20 parts by weight of said basic amino acid or salt thereof, and 1 part by weight of said human growth hormone having a molecular weight of about 20,000.

31. The stable pharmaceutical preparation of claim 25, which further comprises a nonionic surfactant.

32. The stable pharmaceutical preparation of claim 31, wherein said non-ionic surfactant is polysorbate 20 or polysorbate 80.

33. The stable pharmaceutical preparation of claim 25, which further comprises an excipient.

34. The stable pharmaceutical preparation of claim 33, wherein said excipient is a sugar alcohol.

35. The stable pharmaceutical preparation of claim 34, wherein said sugar alcohol is mannitol.

36. The stable pharmaceutical preparation of claim 25, wherein said aqueous solution has a pH ranging from 5 to 8.

37. The stable pharmaceutical preparation of claim 36, wherein said pH is controlled by the addition of a buffer or a pH controlling agent.

38. A stable pharmaceutical preparation which comprises an aqueous solution containing a pharmaceutically effective amount of a human growth hormone having a molecular weight of about 20,000, said preparation comprising (i) a pharmaceutically effective amount of a human growth hormone having a molecular weight of about 20,000; (ii) creatinine; (iii) arginine; (iv) polysorbate 20 or polysorbate 80; and (v) mannitol, wherein the amounts of (ii), (iii), (iv), and (v) are sufficient to enhance the stability and solubility of said human growth hormone in said preparation.

39. A method for producing a stable lyophilized preparation suitable for human administration comprising a human growth hormone having a molecular weight of about 20,000 having reduced insoluble matter, comprising adding to said pharmaceutical preparation an amount of at least one water-soluble heterocyclic compound sufficient to reduce the amount of insoluble matter contained therein and at least one basic amino acid or salt thereof in an amount sufficient to reduce the production of deamidated and sulfoxide variants of said human growth hormone.

40. The method of claim 39, wherein said at least one water-soluble heterocyclic compound is selected from the group consisting of creatinine, an acetyl tryptophan salt, and nicotinamide.

41. The method of claim 40, wherein said compound is creatinine.

42. The method of claim 39, which further comprises an amount of at least one basic amino acid or salt thereof.

43. The method of claim 42, which comprises 1 to 20 parts by weight of said basic amino acid or salt thereof, which is selected from the group consisting of arginine, arginine hydrochloride, lysine, lysine hydrochloride, and histidine.

44. The method of claim 42, which comprises 1 to 20 parts by weight of said basic amino acid or salt thereof, and 1 part by weight of said human growth hormone having a molecular weight of about 20,000.

45. The method of claim 39, which further comprises a nonionic surfactant.

46. The method of claim 45, wherein said nonionic surfactant is polysorbate 20 or polysorbate 80.

47. The method of claim 39, which further comprises an excipient.

48. The method of claim 42, wherein said excipient is a sugar alcohol.

49. The method of claim 48, wherein said sugar alcohol is mannitol.

50. A method for producing a stable lyophilized preparation suitable for human administration comprising a human growth hormone having a molecular weight of about 20,000 having reduced insoluble matter, comprising combining (i) a pharmaceutically effective amount of a human growth hormone having a molecular weight of about 20,000 with amounts of (ii) creatinine; (iii) arginine; (iv) polysorbate 20 or polysorbate 80; and (v) mannitol, wherein the amounts of (ii), (iii), (iv) and (v) are sufficient to enhance the stability and solubility of said human growth hormone in said preparation.

51. A method for producing an aqueous pharmaceutical preparation suitable for human administration comprising a human growth hormone having a molecular weight of about 20,000 having reduced insoluble matter, comprising combining (i) a pharmaceutically effective amount of a human growth hormone having a molecular weight of about 20,000; (ii) water or an aqueous solution; and (iii) at least one water-soluble heterocyclic compound in an amount sufficient to reduce the amount of insoluble matter contained therein; and (iv) at least one basic amino acid or salt thereof in an amount sufficient to reduce the production of deamidated and sulfoxide variants of said human growth hormone.

52. The method of claim 51, wherein said at least one water-soluble heterocyclic compound is selected from the group consisting of creatinine, an acetyl tryptophan salt, and nicotinamide.

53. The method of claim 52, wherein said at least one water-soluble heterocyclic compound is creatinine.

54. The method of claim 51, which further comprises an amount of at least one basic amino acid or salt thereof.

55. The method of claim 54, wherein said basic amino acid or salt thereof is selected from the group consisting of arginine, arginine hydrochloride, lysine, lysine hydrochloride, and histidine.

56. The method of claim 54, which comprises 1 to 20 parts by weight of said basic amino acid or salt thereof, and 1 part by weight of said human growth hormone having a molecular weight of about 20,000.

57. The method of claim 51, which further comprises a nonionic surfactant.

58. The method of claim 57, wherein said nonionic surfactant is polysorbate 20 or polysorbate 80.

59. The method of claim 51, which further comprises an excipient.

60. The method of claim 59, wherein said excipient is a sugar alcohol.

61. The method of claim 60, wherein said sugar alcohol is mannitol.

62. A method for producing an aqueous pharmaceutical preparation suitable for human administration comprising a human growth hormone having a molecular weight of about 20,000 having reduced insoluble matter, wherein said preparation is produced by combining (i) a pharmaceutically effective amount of a human growth hormone having a molecular weight of about 20,000; (ii) water or an aqueous solution, and amounts of (iii) creatinine; (iv) arginine; (v) polysorbate 20 or polysorbate 80; and (vi) mannitol, wherein the amounts of (ii), (iii), (iv) and (v) are sufficient to enhance the stability and solubility of said human growth hormone in said aqueous preparation.

* * * * *

UNITED STATES PATENT AND TRADEMARK OFFICE
CERTIFICATE OF CORRECTION

| | |
|---|---|
| PATENT NO. | : 6,013,773 |
| DATED | : January 11, 2000 |
| INVENTOR(S) | : Hideki Kobayashi et al. |

It is certified that error appears in the above-identified patent and that said Letters Patent is hereby corrected as shown below:

Column 18,
Line 8, change "11" to -- 19 --.

Column 19,
Line 44, change "42" to -- 47 --.

Signed and Sealed this

Second Day of October, 2001

Attest:

*Nicholas P. Godici*

NICHOLAS P. GODICI
*Attesting Officer*    *Acting Director of the United States Patent and Trademark Office*

UNITED STATES PATENT AND TRADEMARK OFFICE
CERTIFICATE OF CORRECTION

PATENT NO.    : 6,013,773
DATED         : January 11, 2000
INVENTOR(S)   : Hideki Kobayashi et al.

It is certified that error appears in the above-identified patent and that said Letters Patent is hereby corrected as shown below:

Title page,
Item [73], delete "Mitsui Chemicals, Inc., Tokyo, Japan" and insert therefor
-- Schering Aktiengesellschaft, Germany --.

Column 7,
Lines 57-58, change "adjustmenting" to -- adjusting --.

Column 8,
Line 25, change "1.25%(11.1mM)" to -- 1.25%(111mM) --.

Column 10,
Line 1, change "increased" to -- raised --.
Line 10, before "reconstitution" insert -- the appearance of solution after --.
Note in Table 5, change "0:good;  O:excellent" to -- O:good; :⊚excellent --.
Lines 47-48, change "increased" to -- raised --.

Column 11,
Line 20, change "controlling" to -- adjusting --.
Line 64, change "increased" to -- raised --.

Column 12,
Line 37, change "increased" to -- raised --.

Column 13,
Line 9, change "increased" to -- raised --.

Column 17,
Line 20, change "controlled" to -- adjusted --.
Line 21, change "pH controlling agent" to -- pH adjusting agent --.

UNITED STATES PATENT AND TRADEMARK OFFICE
CERTIFICATE OF CORRECTION

PATENT NO. : 6,013,773
DATED : January 11, 2000
INVENTOR(S) : Hideki Kobayashi et al.

It is certified that error appears in the above-identified patent and that said Letters Patent is hereby corrected as shown below:

Column 18,
Line 66, change "controlled" to -- adjusted --.
Line 67, change "pH controlling agent" to -- pH adjusting agent --.

Signed and Sealed this

Twenty-fourth Day of September, 2002

Attest:

Attesting Officer

JAMES E. ROGAN
Director of the United States Patent and Trademark Office

SEQUENCE LISTING (1) GENERAL INFORMATION:

(iii) NUMBER OF SEQUENCES: 2

(2) INFORMATION FOR SEQ ID NO:1:

(i) SEQUENCE CHARACTERISTICS:
      (A) LENGTH: 176 amino acids
      (B) TYPE: amino acid
      (C) STRANDEDNESS: single
      (D) TOPOLOGY: linear (ii) MOLECULE TYPE: protein (xi) SEQUENCE DESCRIPTION: SEQ ID NO:1:

```
Phe Pro Thr Ile Pro Leu Ser Arg Leu Phe Asp Asn Ala Met Leu Arg
1               5                   10                  15

Ala His Arg Leu His Gln Leu Ala Phe Asp Thr Tyr Gln Glu Phe Asn
            20                  25                  30

Pro Gln Thr Ser Leu Cys Phe Ser Glu Ser Ile Pro Thr Pro Ser Asn
            35                  40                  45

Arg Glu Glu Thr Gln Gln Lys Ser Asn Leu Glu Leu Leu Arg Ile Ser
        50                  55                  60

Leu Leu Leu Ile Gln Ser Trp Leu Glu Pro Val Gln Phe Leu Arg Ser
65                  70                  75                  80

Val Phe Ala Asn Ser Leu Val Tyr Gly Ala Ser Asp Ser Asn Val Tyr
                85                  90                  95

Asp Leu Leu Lys Asp Leu Glu Glu Gly Ile Gln Thr Leu Met Gly Arg
                100                 105                 110

Leu Glu Asp Gly Ser Pro Arg Thr Gly Gln Ile Phe Lys Gln Thr Tyr
                115                 120                 125

Ser Lys Phe Asp Thr Asn Ser His Asn Asp Asp Ala Leu Leu Lys Asn
            130                 135                 140

Tyr Gly Leu Leu Tyr Cys Phe Arg Lys Asp Met Asp Lys Val Glu Thr
145                 150                 155                 160

Phe Leu Arg Ile Val Gln Cys Arg Ser Val Glu Gly Ser Cys Gly Phe
                165                 170                 175
```

(2) INFORMATION FOR SEQ ID NO:2:

(i) SEQUENCE CHARACTERISTICS:
        (A) LENGTH: 176 amino acids
        (B) TYPE: amino acid
        (C) STRANDEDNESS: single
        (D) TOPOLOGY: linear (ii) MOLECULE TYPE: protein (xi) SEQUENCE DESCRIPTION: SEQ ID NO:2:

```
Phe Pro Thr Ile Pro Leu Ser Arg Leu Phe Asp Asn Ala Ser Leu Arg
1               5                   10                  15

Ala His Arg Leu His Gln Leu Ala Phe Asp Thr Tyr Gln Glu Phe Asn
            20                  25                  30

Pro Gln Thr Ser Leu Cys Phe Ser Glu Ser Ile Pro Thr Pro Ser Asn
            35                  40                  45

Arg Glu Glu Thr Gln Gln Lys Ser Asn Leu Glu Leu Leu Arg Ile Ser
        50                  55                  60

Leu Leu Leu Ile Gln Ser Trp Leu Glu Pro Val Gln Phe Leu Arg Ser
65                  70                  75                  80

Val Phe Ala Asn Ser Leu Val Tyr Gly Ala Ser Asp Ser Asn Val Tyr
                85                  90                  95

Asp Leu Leu Lys Asp Leu Glu Glu Gly Ile Gln Thr Leu Met Gly Arg
                100                 105                 110

Leu Glu Asp Gly Ser Pro Arg Thr Gly Gln Ile Phe Lys Gln Thr Tyr
                115                 120                 125

Ser Lys Phe Asp Thr Asn Ser His Asn Asp Asp Ala Leu Leu Lys Asn
            130                 135                 140

Tyr Gly Leu Leu Tyr Cys Phe Arg Lys Asp Met Asp Lys Val Glu Thr
145                 150                 155                 160

Phe Leu Arg Ile Val Gln Cys Arg Ser Val Glu Gly Ser Cys Gly Phe
                165                 170                 175
```